United States Patent [19]

Katayama et al.

[11] Patent Number: 5,578,552
[45] Date of Patent: Nov. 26, 1996

[54] INDOLE-3-ALKANOIC ACID DERIVATIVES AND USE FOR INCREASING SUGAR CONTENT AND/OR DECREASING ACIDITY IN FRUIT

[75] Inventors: Masato Katayama, Midori-ku; Shozo Fujii, Chikusa-ku; Hiroshi Kimoto, Kuwana; Katsuya Kato, Kita-ku, all of Japan

[73] Assignees: Agency of Industrial Science and Technology,; Ministry of International Trade and Industry, both of Tokyo, Japan

[21] Appl. No.: 336,744

[22] Filed: Nov. 9, 1994

[30] Foreign Application Priority Data

Nov. 9, 1993 [JP] Japan .................... 5-304613

[51] Int. Cl.$^6$ .................... A01N 43/38; C07D 209/18
[52] U.S. Cl. .................... 504/285; 548/494
[58] Field of Search .................... 548/494; 504/285

[56] References Cited

U.S. PATENT DOCUMENTS 3,885,949 5/1975 Ono .................... 71/79

FOREIGN PATENT DOCUMENTS 0256128 2/1988 European Pat. Off. .
5-279331 10/1993 Japan .

OTHER PUBLICATIONS

Collection of Monographs for publication at the 1990 general meeting of the Plant Chemical Regulation Society, p. 31, published by the Plant Chemical Regulation Society.
Growth of Avena Coleoptiles and pH Drop of Protoplast Suspensions Induced by Chlorinated Indole acetic Acids, Michael Bottger, Kjeld C. Engvild and H. Soll, Planta, An International Journal Of Plant Biology, vol. 140, No. 1, 1978, pp. 89–92.

Patent Abstracts of Japan, vol. 15, No. 413 (C–0977), Oct. 22, 1991, JP–A–03 169 858, Jul. 23, 1991.

Chemical Abstracts, vol. 120, No. 19, p. 345, May 9, 1994, K. Kato, et al., "Studies On The Plant Growth Regulators Containing Flourines. Biological Acitivity TFIBA", and Nagoya Kogyo Gijitsu Shikensho Hokuku, vol. 42, No. 8/9, pp. 215–223, 1993.

Database WPI, Derwent Publications, AN 93–374582, JP–A–5 279 331, Oct. 26, 1993.

*Primary Examiner*—David E. Springer
*Attorney, Agent, or Firm*—Oblon, Spivak, McClelland, Maier & Neustadt, P.C.

[57] ABSTRACT

An agent for increasing the sugar content and/or decreasing the acid content of plant fruits has as a substantial main component thereof a fluorine-containing β-indolebutyric acid compound represented by the general formula

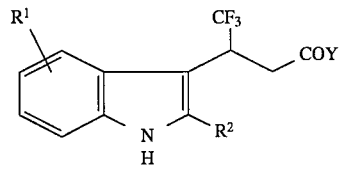

(wherein Y stands for one member selected from the class consisting of hydroxyl group, alkoxy group, amino group, and alkyl amino group and $R^1$ and $R^2$ independently stand for one member selected from the class consisting of hydrogen atom, halogen atom, alkyl group, alkoxy group, aryl group, nitro group, amino group, and alkyl amino group). A method for producing ripe fruits having a high sugar content and/or a low acid content by causing the fluorine-containing β-indolebutyric acid compound mentioned above to adhere to unripe fruits on plants and plants bearing fruits and subsequently allowing the fruits to mature.

20 Claims, No Drawings

INDOLE-3-ALKANOIC ACID DERIVATIVES AND USE FOR INCREASING SUGAR CONTENT AND/OR DECREASING ACIDITY IN FRUIT

BACKGROUND OF THE INVENTION

1. Field of the Invention

This invention relates to an agent for increasing the sugar content and/or decreasing the acid content in plant fruits, which agent has a fluorine-containing β-indolebutyric acid compound as a substantial main component thereof, and to a method for obtaining ripe fruits having a high sugar content and/or a low acid content by causing the fluorine-containing β-indolebutyric acid compound to adhere to unripe fruits, to the environment of plants bearing fruits, or to plants in their entirety, and subsequently allowing the fruits to mature.

2. Description of the Prior Art

The most important requirement for fruits used for luxury consumption in the form of their fresh meats or their extracted juices is abundant sweetness. The sweetness of a fruit is more strongly perceived when the sugar content determined as a physical quantity is large and the acid content similarly determined is small, and the sweetness of a fruit is generally perceived with significant difference when the sugar-acid ratio of the fruit calculated as the ratio of the sugar content to the acid content is higher than that of the compared fruit by one unit.

It is a common practice to treat plants bearing fruits with an agent for decreasing their acid content or an agent for increasing their sugar content for the purpose of imparting increased sweetness to the harvested fruits. Ethyl Kurozeto [sodium 5-chloro-1H-indazol-3-ylacetate or ethyl 5-chloro-1H-indazol-3-ylacetate] has been recognized to be more or less effective as an agent for increasing the sugar content and promoting the coloration of citrus fruits. Among the agents for decreasing the acid content of citrus fruits, lead arsenate is the first to have been registered as an agricultural chemical compound in Japan. It was extensively utilized as an agent for decreasing the acid content of citrus fruits for many years.

Chronic lead arsenate poisoning is, however, known to have caused lung cancer, skin cancer, etc. in large numbers of workers engaged in spraying the agent. In addition, consumers of treated citrus fruits are in danger of suffering oral acute poisoning owing to the lead arsenate remaining on the citrus fruit skin. In 1978, the registration of lead arsenate as an agricultural chemical was canceled in Japan. It is believed that the effect of lead arsenate in decreasing the acid content of citrus fruits arises because this compound disturbs the TCA cycle of not only the fruits but also the whole plant and degrades the level of biosynthesis of citric acid in the plants. The directions attached to lead arsenate packages distributed in the U.S.A., for example, include a warning to the effect that three years' continued use of the compound seriously damages the plants themselves. Even at present, the use of agents which are effective in decreasing acid content is widely recognized as indispensable in the case of citrus fruits of strongly acidic taste. Since no effective substitute for lead arsenate has been developed to date, the use of lead arsenate is still authorized in some countries in spite of the numerous problems of this compound. A strong need is therefore felt for the early development of a substituent which is effective in increasing the sugar content and/or decreasing the acid content in citrus plants and which is safe for the human body.

It is known that 4,4,4-trifluoro-3-(indole-3-)butyric acid, 4,4,4-trifluoro-2-hydroxy-3-(indole-3-)butyric acid, and 4,4,4-trifluoro-3-(indole-3-)butyronitrile have the ability to promote elongation of plant roots (Collection of monographs for publication at the 1990 general meeting of the Plant Chemical Regulation Society, page 31, published by the Plant Chemical Regulation Society). Besides, fluorine-containing indolebutyric acid compounds which are similarly effective are disclosed in Japanese Patent Publication Hei 5(1993)-279331 filed by some of the present inventors.

SUMMARY OF THE INVENTION

This invention was accomplished in response to the aforesaid circumstances and has as its object the provision of a novel agent for increasing the sugar content and/or decreasing the acid content in fruits, which agent is effective in increasing the sugar content and/or decreasing the acid content as in citrus fruits and is safe for human body.

The present inventors continued a study on agents for increasing the sugar content and/or decreasing the acid content of fruits and consequently found that fluorine-containing indolebutyric acid compounds having a specific structure are effective particularly in increasing the sugar content and/or decreasing the acid content of citrus and vitis fruits and are safe for human body. This invention was completed on the basis of this knowledge.

To be specific, this invention concerns an agent for increasing the sugar content and/or decreasing the acid content of plant fruits, which agent has as a substantial main component thereof a fluorine-containing β-indolebutyric acid compound represented by the general formula (1):

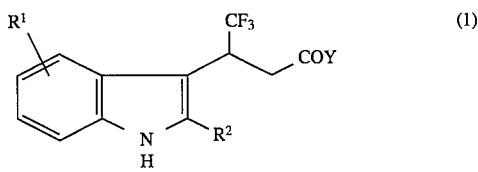

(wherein Y stands for one member selected from the group consisting of hydroxyl group, alkoxy group, amino group, and alkyl amino group and $R^1$ and $R^2$ independently stand for one member selected from the group consisting of hydrogen atom, halogen atom, alkyl group, alkoxy group, aryl group, nitro group, amino group, and alkyl amino group) and a method for producing ripe fruits having a high sugar content and/or a low acid content by causing the fluorine-containing β-indolebutyric acid compound to adhere to unripe fruits on plants and plants bearing fruits and subsequently allowing the fruits to mature.

DESCRIPTION OF THE PREFERRED EMBODIMENTS

A typical example of the method for producing a fluorine-containing β-indolebutyric acid compound represented by the general formula (1) will now be explained.

First, diethyl malonate is dissolved in toluene or benzene, for example, and metallic sodium is placed in the resultant solution and desirably refluxed therein to produce a compound represented by the following formula (2).

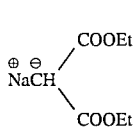

From this compound, the fluorine-containing β-indolebutyric acid compound aimed at by this invention is obtained by the reactions shown below.

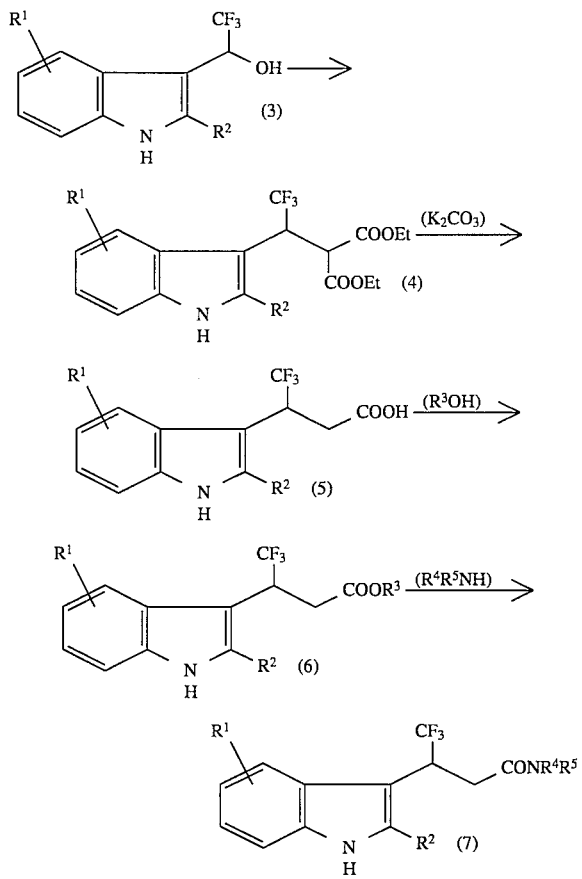

(wherein $R^1$ and $R^2$ have the same meanings as defined above, $R^3$ stands for an alkyl group, and $R^4$ and $R^5$ independently stand for a hydrogen atom or an alkyl group, and Et stands for an ethyl group).

Now, the reactions shown above will be described below.

A diester represented by the formula (4) is obtained by adding 2,2,2-trifluoro-1-(indole-3-)ethanol represented by the formula (3) to a compound represented by the formula (2) and refluxing the resultant mixture. Then, the diester mentioned above is dissolved in a lower alcohol (methanol, for example), combined with the aqueous solution of an alkali carbonate (potassium carbonate, for example), and refluxed to obtain a fluorine-containing β-indolebutyric acid compound represented by the formula (5) [corresponding to formula (1) with OH for Y]. By heating the compound of this invention represented by the formula (5) in conjunction with an alcohol and a catalyst preferably in the presence of an acid, a fluorine-containing β-indolebutyric ester of this invention represented by the formula (6) [corresponding to the formula (1) with $OR^3$ for Y] is obtained. A fluorine-containing β-indolebutyramide of this invention represented by the formula (7) [corresponding to the formula (1) with $NR^4R^3$ for Y] is obtained by heating the compound represented by the formula (6) in conjunction with an amine.

From the practical point of view, the number of carbon atoms in the alkoxy group is desired to be 1 to 5 and that in the alkyl amino group to be 1 to 4 with respect to the substituent Y, the halogen atom is fluorine, chlorine, bromine, or iodine and the number of carbon atoms in the alkyl group is desired to be 1 to 5, that in the alkoxy group to be 1 to 5, that in the aryl group to be 6 to 8, and that in the alkyl amino group to be 1 to 4 with respect to the substituents $R^1$ and $R^2$, the number of carbon atoms in the alkyl group is desired to be 1 to 5 with respect to the substituent $R^3$ and the number of carbon atoms in the alkyl group is desired to be 0 to 4 with respect to the substituents $R^4$ and $R^5$.

The 2,2,2-trifluoro-1-(indole-3-)ethanol represented by the formula (3) shown above can be produced by any of the well-known methods such as are disclosed in the Journal of Fluorine Chemistry, Vol. 39, pp 47 to 59 (1988) and Reports of Government Industrial Research Institute, Nagoya, Vol. 41, pp. 185 to 195 (1992), for example.

Concrete examples of the main fluorine-containing β-indolebutyric acid compounds of the formula (1) which are used in the present invention are shown below.

TABLE 1

| No. | $R^1$ | $R^2$ | Y | Compound | Melting point (°C.) | Yield (%) |
|---|---|---|---|---|---|---|
| 1 | H | H | OH | 4,4,4,-trifluoro-3-(indole-3-)butyric acid | 117–119 | 82.0 |
| 2 | H | H | $OCH_3$ | methyl 4,4,4,-trifluoro-3-(indole-3-)butyrate | 87–88 | |
| 3 | H | H | $OC_2H_5$ | ethyl 4,4,4,-trifluoro-3-(indole-3-)butyrate | 57–58 | 96.0 |
| 4 | H | H | $OC_3H_7$ | propyl 4,4,4,-trifluoro-3-(indole-3-)butyrate | 54–55 | 83.9 |
| 5 | H | H | $OC_3H_7$-iso | isopropyl 4,4,4,-trifluoro-3-(indole-3-)butyrate | 47–48 | 77.4 |
| 6 | H | H | $OC_4H_9$ | butyl 4,4,4,-trifluoro-3-(indole-3-)butyrate | 23–24 | 95.4 |
| 7 | H | $CH_3$ | OH | 4,4,4,-trifluoro-3-(2-methylindole-3-)butyric acid | 148–149 | 77.4 |
| 8 | H | $CH_3$ | $OC_2H_5$ | ethyl 4,4,4,-trifluoro-3-(2-methylindole-3-)butyrate | 71–71.5 | 98.1 |
| 9 | H | $CH_3$ | $OC_3H_7$ | propyl 4,4,4,-trifluoro-3-(2-methylindole-3-)butyrate | 82–83 | 94.1 |
| 10 | H | $CH_3$ | $OC_3H_7$-iso | isopropyl 4,4,4,-trifluoro-3-(2-methylindole-3-)butyrate | 61–62 | 92.3 |
| 11 | H | $CH_3$ | $NH_2$ | 4,4,4,-trifluoro-3-(2-methylindole-3-)butyramide | 177–177.5 | 71.9 |
| 12 | H | $C_6H_5$ | OH | 4,4,4,-trifluoro-3-(2-phenylindole-3-)butyric acid | 165–167 | 56.6 |
| 13 | H | $C_6H_5$ | $OC_2H_5$ | ethyl 4,4,4,-trifluoro-3-(2-phenylindole-3-)butyrate | 114–115 | 88.5 |
| 14 | H | $C_6H_5$ | $OC_3H_7$ | propyl 4,4,4,-trifluoro-3-(2-phenylindole-3-)butyrate | 97–98 | 90.6 |
| 15 | H | $C_6H_5$ | $OC_3H_7$-iso | isopropyl 4,4,4,-trifluoro-3-(2-phenylindole-3-)butyrate | 138–139 | 91.7 |
| 16 | 5-Br | H | OH | 4,4,4,-trifluoro-3-(5-bromoindole-3-)butyric acid | 171–173 | 82.4 |
| 17 | 5-$CH_3$O | H | OH | 4,4,4,-trifluoro-3-(5-methoxyindole-3-)butyric acid | 169–171 | 81.7 |
| 18 | 4-$CH_3$ | H | OH | 4,4,4,-trifluoro-3-(4-methylindole-3-)butyric acid | 146–148 | 75.8 |
| 19 | 5-$CH_3$ | H | OH | 4,4,4,-trifluoro-3-(5-methylindole-3-)butyric acid | 143–145 | 82.0 |

TABLE 1-continued

| No. | R¹ | R² | Y | Compound | Melting point (°C.) | Yield (%) |
|---|---|---|---|---|---|---|
| 20 | 6-CH₃ | H | OH | 4,4,4,-trifluoro-3-(6-methylindole-3-)butyric acid | 137–139 | 87.3 |
| 21 | 7-CH₃ | H | OH | 4,4,4,-trifluoro-3-(7-methylindole-3-)butyric acid | 95–97 | 80.5 |
| 22 | 5-CH₃O-2-CH₃ | H | OH | 4,4,4,-trifluoro-3-(5-methoxy-2-methylindole-3-)butyric acid | 133–134 | 70.5 |

The fluorine-containing β-indolebutyric acid compounds represented by the formula (1) mentioned above which are obtained as described above are effective in increasing the sugar content and/or decreasing the acid content in citrus and vitis fruits in particular and in promoting coloration of the fruits and are much safer for the human body than the lead arsenate which has been heretofore used as an agent for decreasing the acid content of fruits.

The agent for increasing the sugar content and/or decreasing the acid content of fruits according to this invention contains as a substantial main component thereof one or more members selected from the group of fluorine-containing β-indolebutyric acid compounds represented by the aforementioned formula (1). This agent may be applied in its unmodified form to the unripe fruits on plants or to the plants bearing the fruits or may be prepared as mixed with adjuvants normally used in agricultural pesticides for promoting or stabilizing the effect thereof and molded in the form of solution, powder, granules, wettable agent, flowable agent, or emulsion prior to use on fruits or plants.

These prepared agents may be used either in their unmodified form or as suitably diluted with water to a prescribed concentration prior to use.

The fluorine-containing β-indolebutyric acid compound represented by the formula (1) is generally used at a concentration in the approximate range of from 1 to 100 ppm. This concentration is not critical.

The agent for increasing the sugar content and/or decreasing the acid content of fruits according to this invention and the method for using this agent as contemplated by this invention are effective particularly in increasing the sugar content and/or decreasing the acid content of citrus and vitis fruits and also in promoting coloration of these fruits. It is safe for the human body as well.

This invention will now be described more specifically with reference to working examples. Referential Example 1—Preparation of 4,4,4-trifluoro-3-(indole-3-)butyric acid [satisfying formula (1) with OH for Y, H for R¹, and H for R²]:

In a solution of 16.0 g (100 mmol) of diethyl malonate in 50 ml of toluene, 2.3 g of metallic sodium was placed and refluxed for 1.5 hours and then 4.3 g (20 mmol) of 2,2,2-trifluoro-1-(indole-3-)ethanol [satisfying formula (3) with H for R¹ and H for R²] was added. The resultant mixture was further refluxed for 4 hours. The reaction mixture, with water carefully added thereto, was extracted three times with ethyl acetate. Then, the ethyl acetate layer separated by the extract was washed with water and a saturated aqueous solution of sodium chloride, dried with anhydrous sodium sulfate, and concentrated under a reduced pressure to obtain a toluene solution of crude diester of dicarboxylic acid. This solution was distributed to hexane/acetonitrile. The acetonitrile layer consequently obtained was concentrated under a reduced pressure. The crude diester thus obtained was dissolved in 100 ml of methanol. The solution and 80 ml of an aqueous solution of 25.7 g of potassium carbonate added thereto were refluxed for 90 hours.

The solution consequently obtained was neutralized with hydrochloric acid and concentrated under a reduced pressure to expel methanol, alkalinized with an aqueous 4N-sodium hydroxide solution, and then extracted with ethyl acetate. The water layer consequently separated was acidified with hydrochloric acid and extracted with ethyl acetate. The ethyl acetate layer was washed with water and saturated aqueous sodium chloride solution, dried with anhydrous sodium sulfate, and concentrated under a reduced pressure to obtain a crude carboxylic acid. The crude carboxylic acid was refined by means of silica gel column chromatography to obtain 4.2 g (82.0% yield) of 4,4,4-trifluoro-3-(indole-3) butyric acid.

This compound was found to have a melting point of 117° to 119° C. It was subjected to analysis for infrared absorption spectrum, mass spectrum, and ¹H-NMR. The results were as shown below.

$IR\gamma_{max}^{KBr}$ (cm⁻¹): 3430, 1722, 1460, 1438, 1422, 1380, 1326, 1313, 1296, 1280, 1155, 1117, 962, 823, 745, 664, 618

MS (70 ev): 257 (M⁺, 86%) 237 (30) 198 (100), 188 (22)

¹H-NMR (200MHz, TMS, aceton—d₆): 2.95–3.25 (3H, m), 4.35 (1H, m), 7.00–7.25 (2H, m), 7.40–7.55 (2H, m), 7.69 (1H, d, J=7.0 Hz)

REFERENTIAL EXAMPLES 2

Preparation of 4,4,4-trifluoro-3-(2-methyl-indole-3-)butyric acid [satisfying formula (1) with OH for Y, H for R¹, and CH₃ for R²]

In a solution of 88.5 g (555 mmol) of diethyl malonate in 300 ml of toluene, 12.7 g of metallic sodium was placed and refluxed for 2 hours and then 42.3 g (185 mmol) of 2,2,2-trifluoro-1-(2-methylindole-3-)ethanol satisfying formula (3) with H for R¹ and CH₃ for R²] was added. The resultant mixture was refluxed for 20 hours and methanol was added to the refluxed mixture to decompose the unreacted sodium. The reaction mixture was neutralized with 4N-hydrochloric acid. The neutralized solution was concentrated and the concentrated solution was acidified with 4N-hydrochloric acid and extracted four times with ethyl acetate. Then, the ethyl acetate layer was washed with water and a saturated aqueous sodium chloride solution, dried with anhydrous sodium sulfate, and then concentrated under a reduced pressure to obtain oily crude diester of dicarboxylic acid [satisfying formula (4) with H for R¹ and CH₃ for R²]. This crude diester was dissolved in 200 ml of methanol. The methanol solution and a solution of 127.6 g (925 mmol) of potassium carbonate in 100 ml of water added thereto were refluxed for 48 hours. The resultant solution was cooled to room temperature, neutralized with 4N-hydrochloric acid, and concentrated under a vacuum to obtain an aqueous solution. This aqueous solution was alkalinized with an aqueous 4N-sodium hydroxide solution, and treated three times with ethyl acetate. The water layer consequently separated was acidified with 4N-hydrochloric acid and extracted with ethyl acetate. Then, the ethyl acetate layer was washed with water, dried with anhydrous sodium sulfate, and concentrated under a vacuum to obtain crude indolebutyric acid. The crude indolebutyric acid was isolated by means of silica gel column chromatography and recrystallized with ethyl acetate/hexane to obtain 38.8 g (77.4% yield) of 4,4,4-trifluoro-3-(2-methylindole-3-)butyric acid.

This compound was found to have a melting point of 148° to 149° C. It was subjected to analysis for infrared absorption spectrum, mass spectrum, and $^1$H-NMR. The results were as shown below.

IR$\gamma_{max}^{KBr}$ (cm$^{-1}$): 3475, 3420, 3060, 2930, 1713, 1460, 1430, 1310, 1260, 1150, 1110, 1020, 750, 630, 465

MS (70 ev): 271 (M$^+$, 85%) 251 (6) 226 (5) 212 (100), 202 (39), 160 (10), 156 (12), 130 (12)

$^1$H-NMR (200MHZ, TMS, aceton—d$_6$): 2.95–3.25 (3H, m), 4.35 (1H, m), 7.00–7.25 (2H, m), 7.40–7.55 (2H, m), 7.69 (1H, d, J=7.0 and 7.0 Hz)

REFERENTIAL EXAMPLE 3

Preparation of ethyl 4,4,4-trifluoro-3-(indole-3-)butyrate [satisfying formula (1) with OC$_2$H$_5$ for Y, H for R$^1$, and H for R$^2$]

A solution of 5.1 g (20 mmol) of the 4,4,4-trifluoro-3-(indole-3-)butyric acid obtained in Referential Example 1 in 300 ml of ethanol was saturated with hydrochloric acid gas, refluxed overnight, distilled to expel ethanol and hydrochloric acid, and evaporated to dryness. The residue consequently obtained was isolated by means of silica gel column chromatography and then recrystallized with hexane to obtain 5.5 g (96% yield) of ethyl 4,4,4-trifluoro-3-(indole-3-)butyrate.

This compound was found to have a melting point of 57° to 58° C. It was subjected to analysis for infrared absorption spectrum, mass spectrum, and $^1$H-NMR. The results were as shown below.

IR$\gamma_{max}^{KBr}$ (cm$^{-1}$): 3430, 1725, 1468, 1390, 1263, 1161, 1020, 963, 821, 750

MS (70 ev): 285 (M$^+$, 100%) 265 (32) 237 (51) 198 (75)

$^1$H-NMR (90MHz, TMS, aceton—d$_6$): 1.07 (3H, t, J=7.0 Hz), 4.00 (2H, q, J=7.0 Hz), 3.02 and 3.11 [2H, AB—d, J=15.7 and 9.8 (4.7) Hz], 4.35 (1H, d—d—q, J=9.8, 4.7 and 9.3 Hz), 7.68 (1H, m), 7.09 (1H, m), 7.15 (1H, m), 7.43 (1H, m), 7.44 (1H, d, J =2.4 Hz)

REFERENTIAL EXAMPLE 4

Preparation of ethyl 4,4,4-trifluoro-3-(2-methylindole-3-)butyrate [satisfying formula (1) with OC$_2$H$_5$ for Y, H for R$^1$, and CH$_3$ for R$^2$]

A solution of 2.21 g (8.18 mmol) of the 4,4,4-trifluoro-3-(2-methylindole-3-)butyric acid obtained in Referential Example 2 in 50 ml of ethanol and 0.05 ml of concentrated sulfuric acid added thereto were refluxed for 11 hours. The resultant reaction mixture was poured into ice water, and extracted three times with ether. The ether layer consequently separated was washed with water and a saturated aqueous sodium chloride solution, dried with anhydrous sodium sulfate, and then concentrated under a reduced pressure. The oily crude ethyl ester consequently obtained was isolated by means of silica gel column chromatography and recrystallized with carbon tetrachloride/hexane to obtain 2.40 g (98.1% by yield) of ethyl 4,4,4-trifluoro-3-(2-methylindole-3-)butyrate.

This compound was found to have a melting point of 71° to 71.5° C. It was subjected to analysis for infrared absorption spectrum, mass spectrum and $^1$H-NMR. The results were as shown below.

IR$\gamma_{max}^{KBr}$ (cm$^{-1}$): 3360, 1710, 1460, 1420, 1315, 1295, 1265, 1230, 885, 718 650

MS (70 ev): 299 (M$^+$, 100%) 254 (10) 230 (25) 212 (92), 157 (14)

$^1$H-NMR (90MHZ, TMS, aceton—d$_6$): 1.03 (3H, t, J=7.0 HZ), 2.46 (3H, s), 3.16 (2H, d, J=7.2 Hz), 4.01 (2H, q, J=7.0 HZ), 4.27 (1H, t—d, J=10.5 and 7.2 Hz), 6.9 7.6 (4H, m), 10.05 (1H, brs)

REFERENTIAL EXAMPLE 5

Preparation of 4,4,4-trifluoro-3-(2-methylindole-3-)butyramide [satisfying formula (1) with NH$_2$ for Y, H for R$^1$, and CH$_3$ for R$^2$]

A solution of 0.60 g (2.0 mmol) of the ethyl 4,4,4-trifluoro-3-(2-methylindole-3-)butyrate obtained in Referential Example 4 in 5 ml of methanol and 20 ml of an aqueous 28 wt % ammonia solution added thereto were stirred and heated for reaction at −35° C. for 6 hours. The resultant reaction mixture was cooled with ice, combined with a saturated aqueous sodium chloride solution, and extracted four times with ethyl acetate. Then, the ethyl acetate layer consequently separated was washed with a saturated aqueous sodium chloride solution, dried with anhydrous sodium sulfate, and concentrated under a reduced pressure to obtain a substantially pure amide compound. This compound was recrystallized with ethyl acetate/hexane to obtain 0.39 g (71.9% by yield) of 4,4,4-trifluoro-3-(2methylindole-3-)butyramide.

This compound was found to have a melting point of 177° to 177.5° C. It was subjected to analysis for infrared absorption spectrum, mass spectrum, and $^1$H-NMR. The results were as shown below.

IR$\gamma_{max}^{KBr}$ (cm$^{-1}$): 3500, 3380, 3250, 1685, 1675, 1465, 1340, 1260, 1155, 1105, 1025, 755, 445

MS (70 ev): 271 (M$^+$, 14%) 270 (M$^+$, 93%) 250 (34) 226 (17), 213 (14), 212 (100), 211 (21), 201 (9), 158 (25), 157 (14)

$^1$H-NMR (90MHZ, TMS, aceton—d$_6$): 2.40 (3H, s), 3.18 (2H, s), 4.38 (1H, m), 6.29 (1H, brs), 6.9–7.1 (3H, m), 7.2–7.6 (2H, m), 10.08 (1H, brs)

EXAMPLE 1

Biological test on citrus fruit

From a 15-year-old citrus tree (species Okitsu Sosei Unshu) were selected as test specimens three plots A, B and C each consisting of two branches (bearing 7 to 10 fruits per branch). Chemical solutions containing the 4,4,4-trifluoro-3-(indole-3-)butyric acid obtained in Referential Example 1 in concentrations of 100 ppm and 5 ppm was sprayed on plots A and plot B, respectively at the period of initial coloration of the citrus fruit. Nothing was done for plot C at all. After 35 days following the spraying, four well grown fruits were collected from each of the treated branches and the control branch, and tested for fruit weight, degree of coloration, sugar content, and acid content. The results of the test are shown in Table 2 in conjunction with the sugar-acid ratios found by calculation. In the plot using the chemical solution containing the compound at the concentration of 5 ppm, the chemical solution was found to be effective in promoting the coloration of fruits and in increasing the sweetness of the fruits significantly as evidenced by the large sugar-acid ratio exceeding 1.0 as compared with a control plot.

TABLE 2

| Substituents in the formula compound | Concentration (ppm) | Weight of fruits (%) | Degree of coloration (∝ value) | Sugar content (Brix %) | Acid content *1 | Sugar-acid ratio *2 |
| --- | --- | --- | --- | --- | --- | --- |
| $R^1 = R^2 = H$, | 100 | 112.6 | 19.48 | 10.0 | 1.42 | 7.04 |
| Y = OH | 5 | 97.2 | 22.95 | 10.2 | 1.38 | 7.39 |
| Control (no treatment) | | 100.0 (123 g) | 17.00 | 9.5 | 1.50 | 6.33 |

Note *1
Amount of aqueous 0.1 N NaOH solution required for neutralizing 1 ml of juce
Note *2
Ratio of sugar content to acid content

EXAMPLE 2

Biological test on cumquat fruits

Cumquat trees were divided into four plots and equally vigorous branches each bearing about 20 fruits were selected for treatment in the respective plots. One of three chemical solutions containing the 4,4,4-trifluoro-3-(indole-3-)butyric acid obtained in Referential Example 1 at concentrations of 100 ppm, 10 ppm, and 1 ppm was sprayed on three branches in each plot at the period of initial coloration. After 50 days following the spraying, all the fruits were simultaneously collected. From the total of 30 fruit/plots, 25 fruit/plots having neither flaw nor disease were selected and tested for weight of fruit, degree of coloration, sugar content, and acid content. The results are shown in Table 3 in conjunction with the sugar-acid ratios found by calculation. In the plots using the chemical solutions containing the compound at the concentration of 10 ppm and 100 ppm, the chemical solutions were found to be effective in notably promoting the coloration of the fruits and in increasing the sugar-acid ratio owing to an increase in the sugar content and a marked decrease in the acid content.

Example 1 at concentrations of 50 ppm and 5 ppm was liberally sprayed on five bunches each consisting of 35 to 40 uniformly grown grape berries and two or three leaves above and below each bunch at the period of initial coloration due to ripening. Covering bags were removed from the bunches before the spraying and were replaced after the sprayed solution had dried. The grape berries were then cultivated under ordinary controlled conditions. 25 days following the spraying, the treated bunches and the control bunches were simultaneously harvested and tested for weight of fruit, degree of coloration, sugar content, and acid content. The results are shown in Table 4 in conjunction with the sugar-acid ratios found by calculation. In the plot using the chemical solution containing the compound at a concentration of 50 ppm, the chemical solution was found to promote the coloration of the grape berries due to ripening and, in consequence of the progress of this coloration, notably increase the sugar-acid ratio due to an increase in the sugar content and a conspicuous decrease in the acid content.

TABLE 3

| Substituents in the formula compound | Concentration (ppm) | Weight of fruits (%) | Degree of coloration (∝ value) | Sugar content (Brix %) | Acid content *1 | Sugar-acid ratio *2 |
| --- | --- | --- | --- | --- | --- | --- |
| $R^1 = R^2 = H$, | 100 | 104.0 | 16.72 | 13.7 | 1.61 | 8.51 |
| Y = OH | 10 | 107.9 | 18.24 | 13.9 | 1.57 | 8.85 |
| | 1 | 98.7 | 13.51 | 13.1 | 1.88 | 6.96 |
| Control (no treatment) | | 100.0 (6.08 g/berry) | 12.05 | 12.7 | 1.94 | 6.65 |

Note *1
Amount of aqueous 0.1 N NaOH solution required for neutralizing 1 ml of juce
Note *2
Ratio of sugar content to acid content

EXAMPLE 3

Biological test on grape berries

Grape vines (species Kyoho) were divided into three plots and one of two chemical solutions containing the 4,4,4-trifluoro-3-(indole-3-)butyric acid obtained in Referential

TABLE 4

| Substituents in the formula compound | Concentration (ppm) | Weight of berries (%) | Degree of coloration (∝ value) | Sugar content (Brix %) | Acid content *1 | Sugar-acid ratio *2 |
|---|---|---|---|---|---|---|
| $R^1 = R^2 = H$, | 50 | 101.2 | 6.4 | 13.4 | 1.63 | 8.22 |
| Y = OH | 5 | 103.6 | 4.3 | 12.4 | 1.90 | 6.53 |
| Control (no treatment) | | 100.0 (13.1 g) | 4.1 | 12.5 | 1.90 | 6.55 |

Note *1
Amount of aqueous 0.1 N NaOH solution required for neutralizing 1 ml of juce
Note *2
Ratio of sugar content to acid content It is obvious from the test results given above that the fluorine-containing β-indolebutyric acid type agent for increasing the sugar content and/or decreasing the acid content in fruits, which agent contains one or more fluorine-containing β-indolebutyric acid compounds represented by the formula (1), combines the ability to increase the sugar content with the ability to decrease the acid content in fruits. The agent manifests its ability to promote coloration and its ability to markedly increase sugar content and/or decrease acid content particularly with respect to citrus and vitis fruits.

What is claimed is:

1. A composition for increasing the sugar content and/or decreasing the acid content of plant fruits, which agent has as a substantial main component thereof an effective amount of a fluorine-containing β-indolebutyric acid compound represented by the general formula:

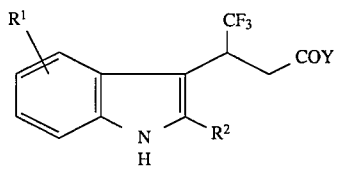

wherein Y stands for one member selected from the group consisting of hydroxyl group, alkoxy group, amino group, and alkyl amino group and $R^1$ and $R^2$ independently stand for one member selected from the group consisting of hydrogen atom, halogen atom, alkyl group, alkoxy group, aryl group, nitro group, amino group, and alkyl amino group and an agriculturally acceptable carrier, diluent or adjuvant.

2. A composition according to claim 1, wherein said plant is one member selected from the group consisting of citrus and vitis.

3. A composition according to claim 1, wherein said principal main component is one member selected from the group consisting of 4,4,4-trifluoro-3-(indole-3-)butyric acid, methyl 4,4,4-trifluoro-3-(indole-3-) butyrate, ethyl 4,4,4-trifluoro-3-(indole-3-)butyrate, propyl 4,4,4-trifluoro-3-(indole-3-)butyrate, isopropyl 4,4,4-trifluoro-3-(indole-3-)butyrate, butyl 4,4,4-trifluoro-3-(indole-3-)butyrate, 4,4,4-trifluoro-3-(2-methylindole-3-)butyric acid, ethyl 4,4,4-trifluoro-3-(2-methylindole-3-)butyrate, propyl 4,4,4-trifluoro-3-(2-methylindole-3-)butyrate, isopropyl 4,4,4-trifluoro-3-(2-methylindole- 3-)butyrate, 4,4,4-trifluoro-3-(2-methylindole-3-)butyramide, 4,4,4-trifluoro-3-(2-phenylindole-3-)butyric acid, ethyl 4,4,4-trifluoro-3-(2-phenylindole-3-)butyrate, propyl 4,4,4-trifluoro-3-(2-phenylindole-3-)butyrate, isopropyl 4,4,4-trifluoro-3-(2-phenylindole-3-)butyrate, 4,4,4-trifluoro-3-(5-bromoindole-3-)butyric acid, 4,4,4-trifluoro-3-(5-methoxyindole-3) butyric acid, 4,4,4-trifluoro-3-(4-methylindole-3-)butyric acid, 4,4,4-trifluoro-3-(5-methylindole-3-)butyric acid, 4,4,4-trifluoro-3-(6-methylindole-3-)butyric acid, 4,4,4-trifluoro-3-(7-methylindole-3-)butyric acid, and 4,4,4-trifluoro-3-(5-methoxy-2-methylindole-3-)butyric acid.

4. A method for producing ripe fruits having a high sugar content and/or a low acid content by causing a fluorine-containing β-indolebutyric acid compound represented by the general formula:

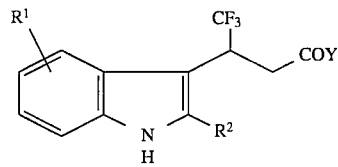

(wherein Y stands for one member selected from the class consisting of hydroxyl group, alkoxy group, amino group, and alkyl amino group and $R^1$ and $R^2$ independently stand for one member selected from the class consisting of hydrogen atom, halogen atom, alkyl group, alkoxy group, aryl group, nitro group, amino group, and alkyl amino group) to adhere to unripe fruits on plants and plants bearing fruits and subsequently allowing the fruits to mature.

5. A method according to claim 4, wherein said plant is one member selected from the group consisting of citrus and vitis.

6. A method according to claim 4, wherein said substantial main component is one fluorine-containing β-indolebutyric acid compound selected from the group consisting of 4,4,4-trifluoro-3-(indole-3-)butyric acid, methyl 4,4,4-trifluoro-3-(indole-3-)butyrate, ethyl 4,4,4-trifluoro-3-(indole-3-)butyrate, propyl 4,4,4-trifluoro-3-(indole-3-)butyrate, isopropyl 4,4,4-trifluoro-3-(indole-3-)butyrate, butyl 4,4,4-trifluoro-3-(indole-3-) butyrate, 4,4,4-trifluoro-3-(2-methylindole-3-)butyric acid, ethyl 4,4,4-trifluoro-3-(2-methylindole-3-)butyrate, propyl 4,4,4-trifluoro-3-(2-methylindole-3-)butyrate, isopropyl 4,4,4-trifluoro-3-(2-methylindole-3-)butyrate, 4,4,4-trifluoro-3-(2-methylindole-3-)butyramide, 4,4,4-trifluoro-3-(2-phenylindole-3-)butyric acid, ethyl 4,4,4-trifluoro-3-(2-phenylindole-3-)butyrate, propyl 4,4,4-trifluoro-3-(2-phenylindole-3-)butyrate, isopropyl 4,4,4-trifluoro-3-(2-phenylindole-3-)butyrate, 4,4,4-trifluoro-3-(5-bromoindole-3-)butyric acid, 4,4,4-trifluoro-3-(5-methoxyindole-3) butyric acid, 4,4,4-trifluoro-3-(4-methylindole-3-)butyric acid 4,4,4-trifluoro-3-(5-methylindole-3-)butyric acid, 4,4,4-trifluoro-3-(6-methylindole-3-)butyric acid, 4,4,4-trifluoro-3-(7-methylindole-3-)butyric acid, and 4,4,4-trifluoro-3-(5-methoxy-2-methyylindole-3-)butyric acid.

7. The composition of claim 1, wherein Y is $C_{1-5}$ alkoxy.

8. The composition of claim 1, wherein Y is $C_{1-4}$ alkyl.

9. The composition of claim 1, wherein $R^1$ or $R^2$ is fluorine, chlorine, bromine or iodine.

10. The composition of claim 1, wherein $R^1$ or $R^2$ is $C_{1-5}$ alkyl.

11. The composition of claim 1, wherein $R^1$ or $R^2$ is $C_{1-5}$ alkoxy.

12. The composition of claim 1, wherein $R^1$ or $R^2$ is $C_{6-8}$ aryl.

13. The composition of claim 1, wherein $R^1$ or $R^2$ is $C_{1-4}$ alkylamino.

14. The method of claim 4, wherein Y is $C_{1-5}$ alkoxy.

15. The method of claim 4, wherein Y is $C_{1-4}$ alkyl.

16. The method of claim 4, wherein $R^1$ or $R^2$ is fluorine, chlorine, bromine or iodine.

17. The method of claim 4, wherein $R^1$ or $R^2$ is $C_{1-5}$ alkyl.

18. The method of claim 4, wherein $R^1$ or $R^2$ is $C_{1-5}$ alkoxy.

19. The method of claim 4, wherein $R^1$ or $R^2$ is $C_{6-8}$ aryl.

20. The method of claim 4, wherein $R^1$ or $R^2$ is $C_{1-4}$ alkylamino.

* * * * *

UNITED STATES PATENT AND TRADEMARK OFFICE
CERTIFICATE OF CORRECTION

PATENT NO. : 5,578,552
DATED : November 26, 1996
INVENTOR(S) : Masato KATAYAMA, et al.

It is certified that error appears in the above-indentified patent and that said Letters Patent is hereby corrected as shown below:

On the title page, Item [73], the assignee, should read:

--Agency of Industrial Science & Technology, Ministry of International Trade & Industry--

Signed and Sealed this

Twenty-fifth Day of February, 1997

Attest:

BRUCE LEHMAN

*Attesting Officer*     *Commissioner of Patents and Trademarks*